US007879039B2

(12) United States Patent
Perez-Cruet et al.

(10) Patent No.: US 7,879,039 B2
(45) Date of Patent: Feb. 1, 2011

(54) MINIMALLY INVASIVE INTERSPINOUS PROCESS SPACER INSERTION DEVICE

(75) Inventors: Miquelangelo J. Perez-Cruet, Bloomfield, MI (US); John R. Pepper, Cheshire, CT (US); John A. Miller, Bloomfield Village, MI (US)

(73) Assignee: MI4Spine, LLC, Bloomfield Hills, MI (US)

( * ) Notice: Subject to any disclaimer, the term of this patent is extended or adjusted under 35 U.S.C. 154(b) by 642 days.

(21) Appl. No.: 11/646,749

(22) Filed: Dec. 28, 2006

(65) Prior Publication Data

US 2008/0161822 A1 Jul. 3, 2008

(51) Int. Cl.
*A61B 17/88* (2006.01)

(52) U.S. Cl. .................. 606/86 A; 606/249; 606/99

(58) Field of Classification Search ............ 606/86 A, 606/90, 96, 99, 100, 105, 247–249, 279, 606/86 R, 246; 623/17.11; 604/170.03
See application file for complete search history.

(56) References Cited

U.S. PATENT DOCUMENTS

| 5,314,432 | A * | 5/1994 | Paul .................. 606/130 |
| 7,029,473 | B2 | 4/2006 | Zucherman et al. |
| 7,594,912 | B2 * | 9/2009 | Cooper et al. ............. 606/1 |
| 7,621,918 | B2 * | 11/2009 | Jackson ............... 606/86 A |
| 2005/0021031 | A1 * | 1/2005 | Foley et al. ............. 606/61 |
| 2005/0033315 | A1 * | 2/2005 | Hankins ............... 606/129 |
| 2005/0075634 | A1 | 4/2005 | Zucherman et al. |
| 2005/0154389 | A1 * | 7/2005 | Selover et al. ........... 606/61 |
| 2006/0079894 | A1 * | 4/2006 | Colleran et al. .......... 606/61 |
| 2006/0111713 | A1 * | 5/2006 | Jackson ................ 606/61 |
| 2006/0149278 | A1 * | 7/2006 | Abdou ................ 606/90 |
| 2006/0195102 | A1 * | 8/2006 | Malandain .............. 606/72 |
| 2006/0293662 | A1 | 12/2006 | Boyer, II et al. |
| 2007/0276373 | A1 * | 11/2007 | Malandain .............. 606/61 |
| 2008/0221586 | A1 * | 9/2008 | Garcia-Bengochea et al. ................ 606/108 |
| 2009/0131986 | A1 * | 5/2009 | Lee et al. .............. 606/247 |

OTHER PUBLICATIONS www.fda.gov, CDRH Conosumer Information, New Device Approval, X STOP® Interspinous Process Decompression System (XSTOP)—P040001, 2 pgs.

* cited by examiner

*Primary Examiner*—Eduardo C Robert
*Assistant Examiner*—Steven J Cotroneo
(74) *Attorney, Agent, or Firm*—John A. Miller; Miller IP Group, PLC

(57) ABSTRACT

An interspinous process spacer insertion device that positions an interspinous process spacer between the spinous process of adjacent vertebrae in a minimally invasive percutaneous surgical procedure. The device includes a trocar rod that extends through a cannulated sleeve. The spacer is attached to the end of the cannulated sleeve, where a trocar tip of the trocar rod extends through the spacer. The trocar rod is moved through the cannulated sleeve and an incision in the patient, and is positioned between the spinous process of the vertebra to align the device. The cannulated sleeve is then moved down the trocar rod so that the spacer slides between the spinous process, and the trocar rod is then withdrawn from the patient. The spacer is then rotated so that it locks behind the spinous process, and the cannulated sleeve is detached from the spacer and removed from the patient.

18 Claims, 6 Drawing Sheets

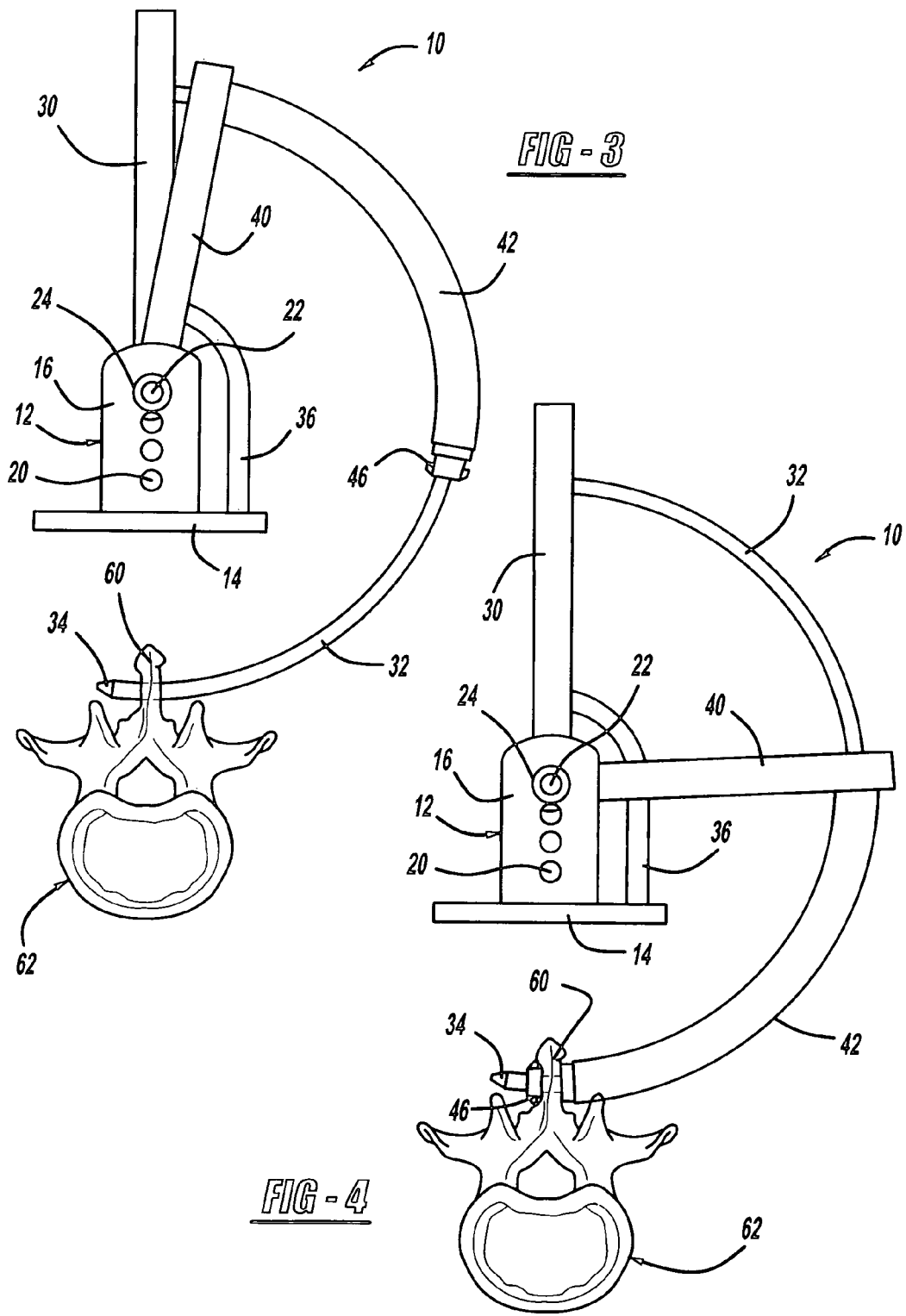

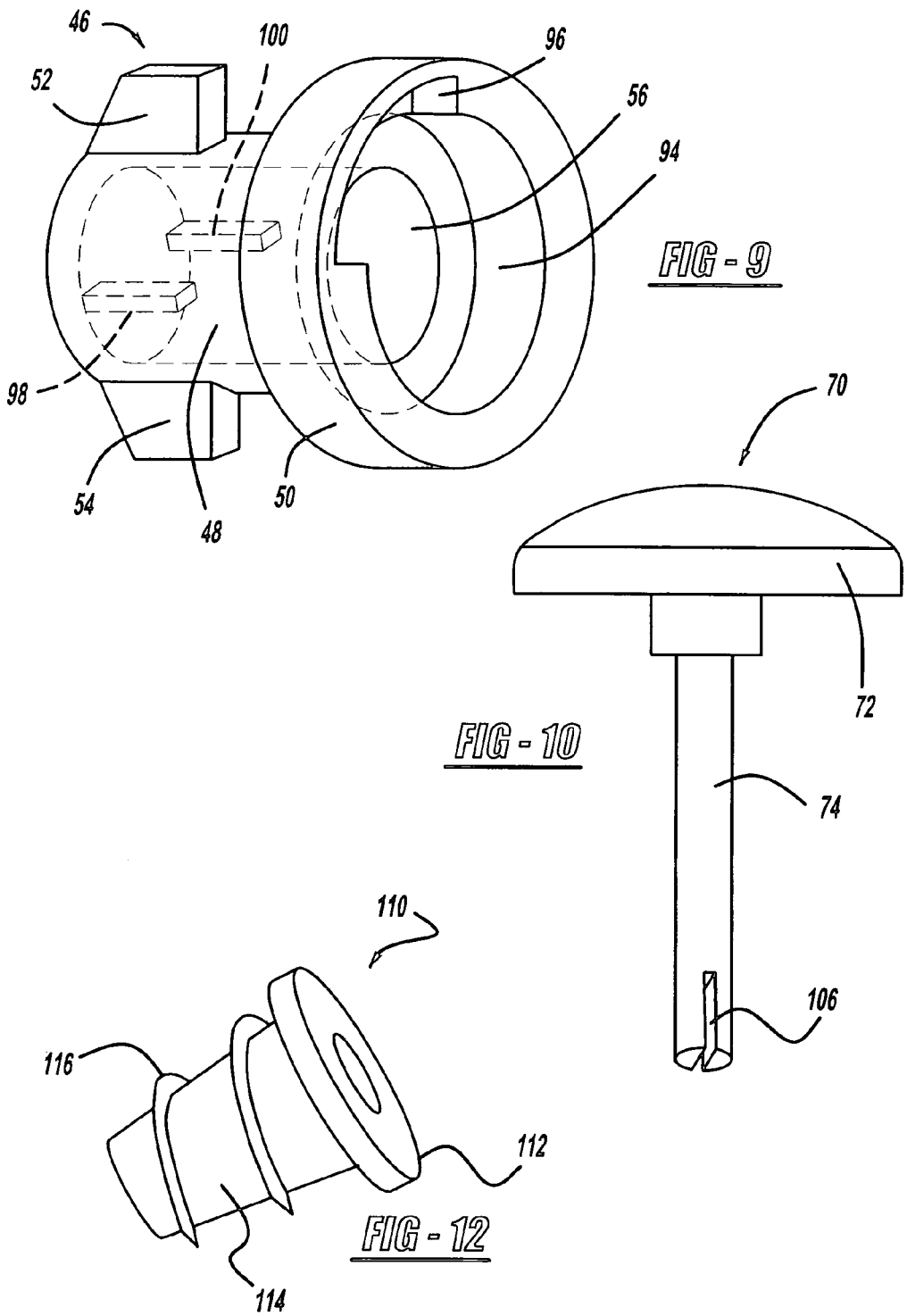

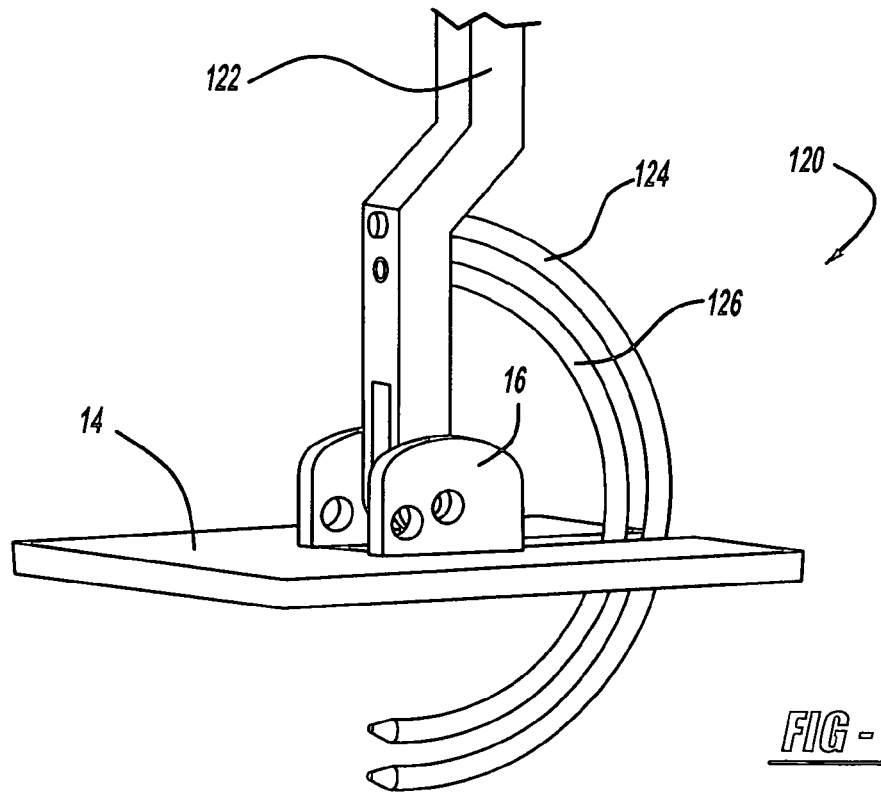
FIG-11
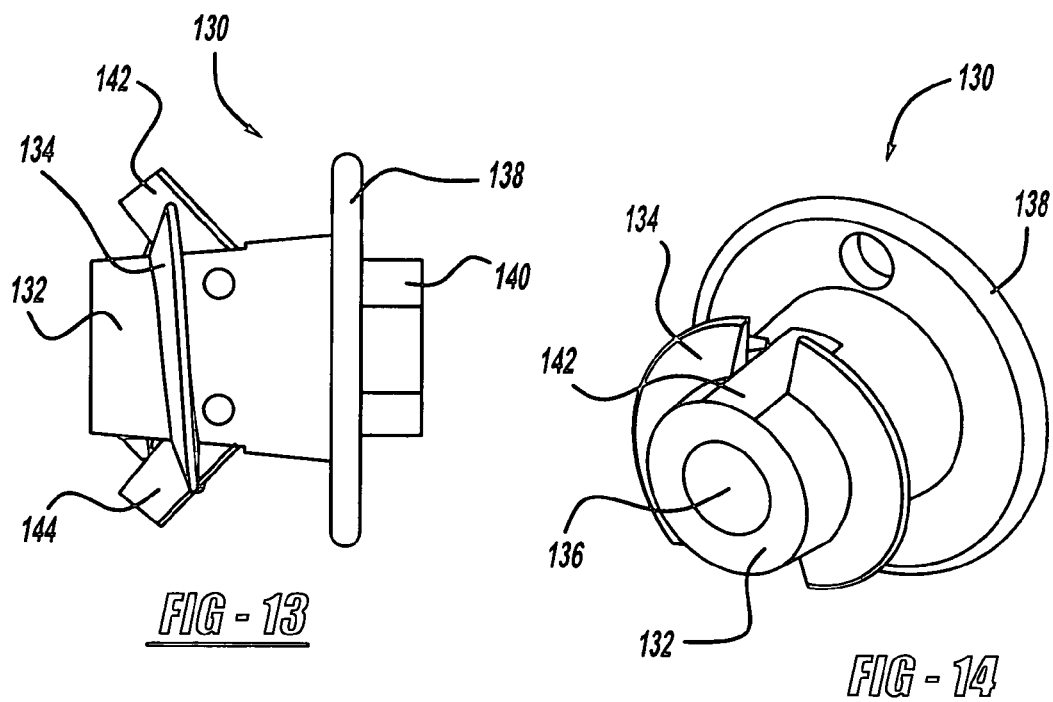
FIG-13
FIG-14

MINIMALLY INVASIVE INTERSPINOUS PROCESS SPACER INSERTION DEVICE

BACKGROUND OF THE INVENTION

1. Field of the Invention

This invention relates generally to a device for inserting a spacer between the spinous process of adjacent vertebrae and, more particularly, to an interspinous process spacer insertion device that percutaneously inserts a spacer between the spinous process of adjacent vertebrae using minimally invasive surgical procedures.

2. Discussion of the Related Art

The human spine includes a series of vertebrae interconnected by connective tissue referred to as discs that act as a cushion between the vertebrae. The discs allow for movement of the vertebrae so that the back can bend and rotate. The vertebra includes a bony spinous process that protrudes towards the back.

The intervertebral disc is an active organ in which the normal and pathologic anatomies are well known, but the normal and pathologic physiologies have not been greatly understood. The intervertebral disc permits rhythmic motions required of all vertebrate animals in their various forms of locomotion. The disc is a high-pressure system composed primarily of absorbed water, an outer multilayered circumferential annulus of strong, flexible, but essentially inelastic collagen fibers, and an inner core of a hydrogel called the nucleus pulposus. The swelling of the contained hydrogel creates the high pressure that tightens the annular fibers and its laminations. Degeneration of discs in humans is typically a slow, complex process involving essentially all of the mechanical and physiologic components with loss of water holding capacity of the disc. Discogenic pain arises from either component, but is primarily due to altered chemistry. When this pain is severely disabling and unyielding, the preferred contemporary treatments are primarily surgical, particularly fusion and/or disc replacement.

Annular collagen fibers are arranged in circumferential belts or laminations inserting strongly and tangentially in right- and left-handed angulated patches into each adjacent vertebral body. Inside the annular ring is contained an aggrecan, glycosaminoglycan, a protein-sugar complex gel having great hygroscopic ability to hold water. The swelling pressure of this gel of the nucleus maintains the pressure within the annulus, forcing the vertebrae apart and tightening the annular fibers. This tightening provides the primary mechanical stability and flexibility of each disc of the spinal column. Further, the angulated arrangement of the fibers also controls the segmental stability and flexibility of the motion segment. Therefore, the motion of each segment relates directly to the swelling capacity of the gel and secondarily to the tightness of intact annulus fibers. The same gel is also found in thin layers separating the annular laminar construction, providing some apparent elasticity and separating the laminations, reducing interlaminar torsional abrasion. With aging or degeneration, nucleus gel declines, while collagen content, including fibrosis, increases.

Disc degeneration, which involves matrix, collagen and aggrecan, usually begins with annular tears or alterations in the endplate nutritional pathways by mechanical or pathophysiologic means. However, the disc ultimately fails for cellular reasons. As a person ages, the discs in the spine go through a degenerative process that involves the gradual loss of the water holding capacity of the disc, referred to as desiccation. As a result of this loss of water, the disc space height may partially collapse, which may lead to chronic back pain disorders and/or leg pain as a result of the nerves being pinched.

Progressive injury and aging of the disc occurs normally in later life and abnormally after trauma or metabolic changes. In addition to the chemical effects on the free nerve endings as a source of discogenic pain, other degenerative factors may occur. Free nerve endings in the annular fibers may be stimulated by stretching as the disc degenerates, bulges, and circumferential delamination of annular fibers occurs. This condition may lead to a number of problems, such as back pain. It has been shown that a person's disc is typically taller in the morning when a person awakes. This phenomenon may be due in part to the reduction of body weight forces on the disc when lying in a recumbent position overnight that causes the disc height to restore. Therefore, reduction of compressive forces on the disc may help to restore disc space height.

As discussed above, as a person ages, the discs of the spine degenerate, and the disc space height collapses. Further, the ligaments and facets of the spine degenerate as well. These problems lead to a reduction in the foramenal height of the vertebrae, often causing central or lateral canal stenosis. The foramen is the opening between the vertebrae that allows the nerve from the spinal cord to pass through. Because the nerve passes through the foramen, the nerve will often get pinched leading to various types of back pain. Further, these problems often lead to difficulty to walking. Additionally, the lateral canal stenosis causes the nerve to get pinched in the spinal canal. These conditions often lead to neurogenic claudication, where the patient typically responds by walking shorter distances, then sitting down, and then flexing the spine by leaning over or by walking with the aid of a device, which helps to flex the spine.

Current surgical procedures that exist for addressing this pathology require that the ligaments and bone that are causing the compression be removed surgically to take the pressure off of the nerves. Recently, interspinous process spacers, such as the X-stop, have been developed. Known interspinous process spacers operate by flexing the spine and opening the canal, lateral recess and foramen to take pressure off of the nerves. These devices typically can be useful for conditions of lateral recess stenosis or foramenal stenosis alone. These devices can also be potentially useful as an adjunct to minimally invasive laminectomy for stenosis where the spinous process is preserved. Interspinous process spacers can act as an adjunct device to minimally invasive laminectomy for stenosis to treat the foramenal stenosis component of this disorder. Following minimally invasive lumbar laminectomy for stenosis, the interspinous process spacer could be placed between the preserved spinous processes of the spine. The result would be to address and treat the lateral or foramenal stenosis that could persist despite the decompression of the spinal canal.

SUMMARY OF THE INVENTION

In accordance with the teachings of the present invention, an interspinous process spacer insertion device is disclosed that positions an interspinous process spacer between the spinous process of adjacent vertebrae in a minimally invasive percutaneous surgical procedure. The device includes a trocar rod that extends through a cannulated sleeve. The spacer is attached to the end of the cannulated sleeve, where a trocar tip of the trocar rod extends through the spacer. The trocar rod is moved through the cannulated sleeve and an incision in the patient, and is positioned between the spinous process of the vertebra to align the device. The cannulated sleeve is then moved down the trocar rod so that the spacer slides between the spinous process, and the trocar rod is then withdrawn from the patient. The spacer is then rotated so that it locks behind the spinous process, and the cannulated sleeve is detached from the spacer and removed from the patient.

Additional features of the present invention will become apparent from the following description and appended claims, taken in conjunction with the accompanying drawings.

BRIEF DESCRIPTION OF THE DRAWINGS

FIG. 3 is a side view of the device depicted in FIG. 1 showing an advanced arced trocar rod;

FIG. 4 is a side view of the device depicted in FIG. 1 showing an advanced curved cannulated sleeve;

FIG. 9 is another perspective view of the interspinous process spacer;

FIG. 10 is a side view of the flexible driver shown in FIG. 6;

FIG. 11 is a perspective view of a minimally invasive interspinous process spacer insertion device including two advanced arced trocar rods, according to another embodiment of the present invention;

FIG. 12 is a perspective view of an interspinous process spacer, according to another embodiment of the present invention; and FIG. 13 is a perspective view and FIG. 14 is a side view of an interspinous process spacer, according to another embodiment of the present invention.

DETAILED DESCRIPTION OF THE EMBODIMENTS

The following discussion of the embodiments of the invention directed to a minimally invasive interspinous process spacer insertion device for positioning an interspinous process spacer between the spinous process of adjacent vertebra is merely exemplary in nature, and is in no way intended to limit the invention or its applications or uses.

Figure 1:
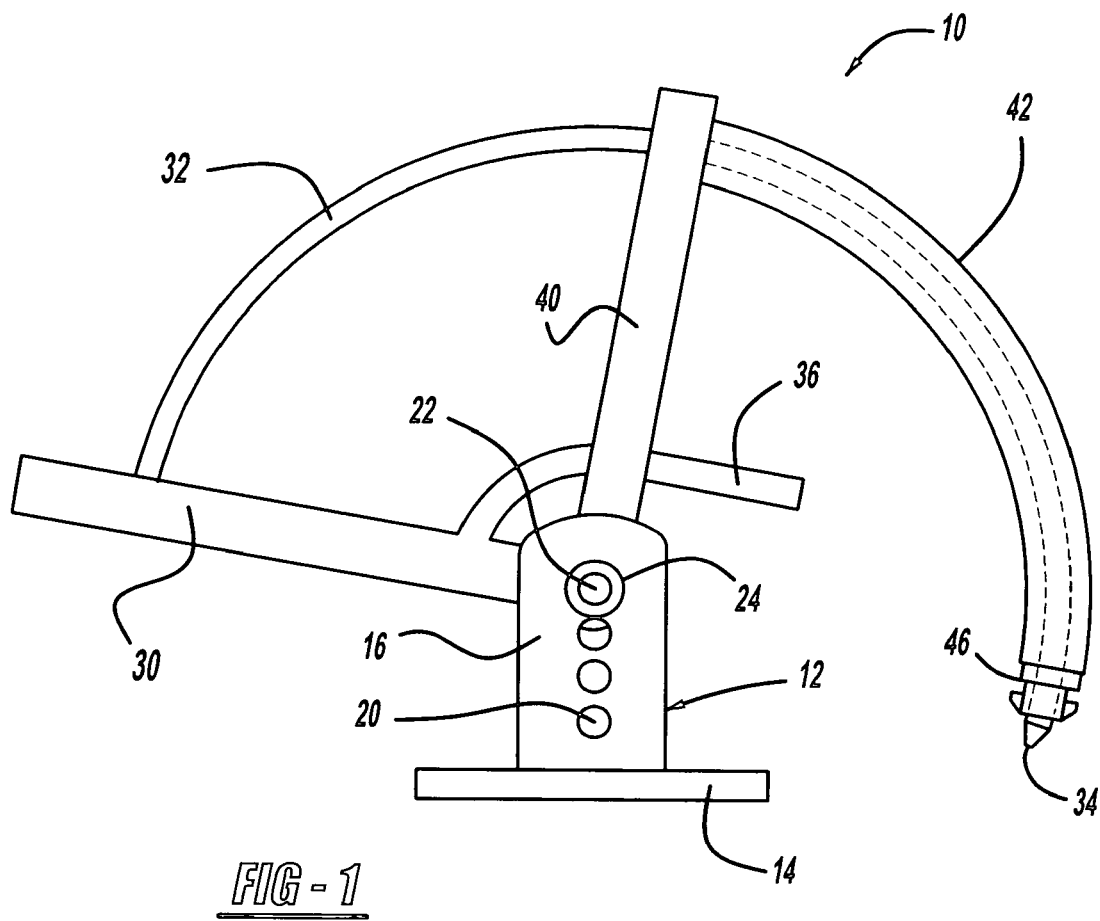
FIG. 1 is a side view of a minimally invasive interspinous process spacer insertion device in a retracted position, according to an embodiment of the present invention.

FIG. 1 is a side view of a minimally invasive interspinous process spacer insertion device 10, according to an embodiment of the present invention. As will be discussed in detail below, the device 10 is used to insert an interspinous process spacer between the interspinous process of adjacent vertebrae in a minimally invasive surgical procedure to provide a minimally invasive surgical solution to foramenal stenosis and/or lateral canal stenosis by preventing the foramen and lateral canal from compressing. The device 10 preserves the muscle attachments to the spine, as well as integrity of the interspinous process ligament, and can be potentially performed under local anesthesia.

The device 10 includes a base portion 12 having a base plate 14 and a pair of opposing spaced apart plate stanchions 16. The stanchions 16 include a series of holes 20 that provide a height adjustment for the device 10, as will become apparent from the discussion below. A support rod 22 including a knob 24 is inserted within opposing holes 20 in the stanchions 16. The support rod 22 also extends through a hole in a cylindrical trocar arm 30 so that the trocar arm 30 is rotatably movable relative to the base portion 12. The trocar arm 30 includes an arced trocar rod 32 having a trocar tip 34. The trocar rod 32 is removably mounted to the trocar arm 30 in any suitable manner, such as by threads, snap fit, etc. The trocar arm 30 also includes a hard stop arm 36 that will contact the base plate 14 to prevent the trocar rod 32 from advancing beyond a maximum position.

The device 10 also includes a cylindrical cannulated arm 40 having an opening (not shown) through which the support rod extends so that the arm 40 is also rotatably mounted to the base portion 12. The cannulated arm 40 also includes another opening (not shown) through which the hard stop arm 36 can move. An arced cannulated sleeve 42 is rigidly coupled to the arm 40, and has the same curvature as the trocar rod 32. The cannulated sleeve 42 has a central bore through which the arced trocar rod 32 is positioned. An interspinous process spacer 46 is rotatably mounted to an end of the cannulated sleeve 42.

Figure 2:
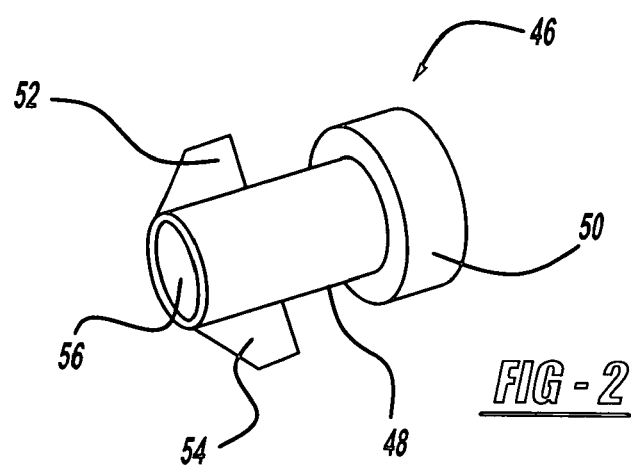
FIG. 2 is a perspective view of an interspinous process spacer, according to an embodiment of the present invention.

FIG. 2 is a perspective view of the spacer 46 removed from the cannulated sleeve 42. The spacer 46 includes a cylindrical body portion 48 and an end plate 50, where the body portion 48 has an internal bore 56. A pair of locking fins 52 and 54 are mounted to the body portion 48 opposite to the end plate 50, as shown. The spacer 46 can be made of any suitable material, such as a rigid plastic that is a single molded piece. In one embodiment, the spacer is radiolucent so that it is visible on an X-ray so that the surgeon can determine if the spacer 46 is in the proper location.

FIG. 3 is a side view of the device 10 showing a first step of the surgical procedure. The base portion 12 is aligned with a patient's spine by any suitable process, where the base plate 14 rests on the patient's back. During the alignment process, using, for example, fluoroscopy and a K-wire, well known to those skilled in the art, the height of the device 10 is adjusted by selecting the proper hole 20 for the arms 30 and 40. An incision is made in the patient lateral to the spine and relative to the base portion 12. The trocar arm 30 is raised so that the sharp trocar tip 34 is inserted through the incision and transverses the soft tissue and muscle of the patient so that the tip 34 extends between the spinous process 60 of adjacent vertebrae 62, as shown.

FIG. 4 shows a next step in the surgical procedure after the arm 32 has been extended between the spinous process 60. The surgeon will then rotate the arm 40 so that the cannulated sleeve 42 moves the spacer 46 down the trocar rod 32. The spacer 46 is coupled to the cannulated sleeve 42 so that the fins 52 and 54 are aligned in the proper orientation so that they easily slide between the spinous process 60. The spacer 46 is in the proper position, as shown in FIG. 4, when the fins 52 and 54 are on one side of the spinous process 60 and the end plate 50 is on the other side of the spinous process 60.

Figure 5:
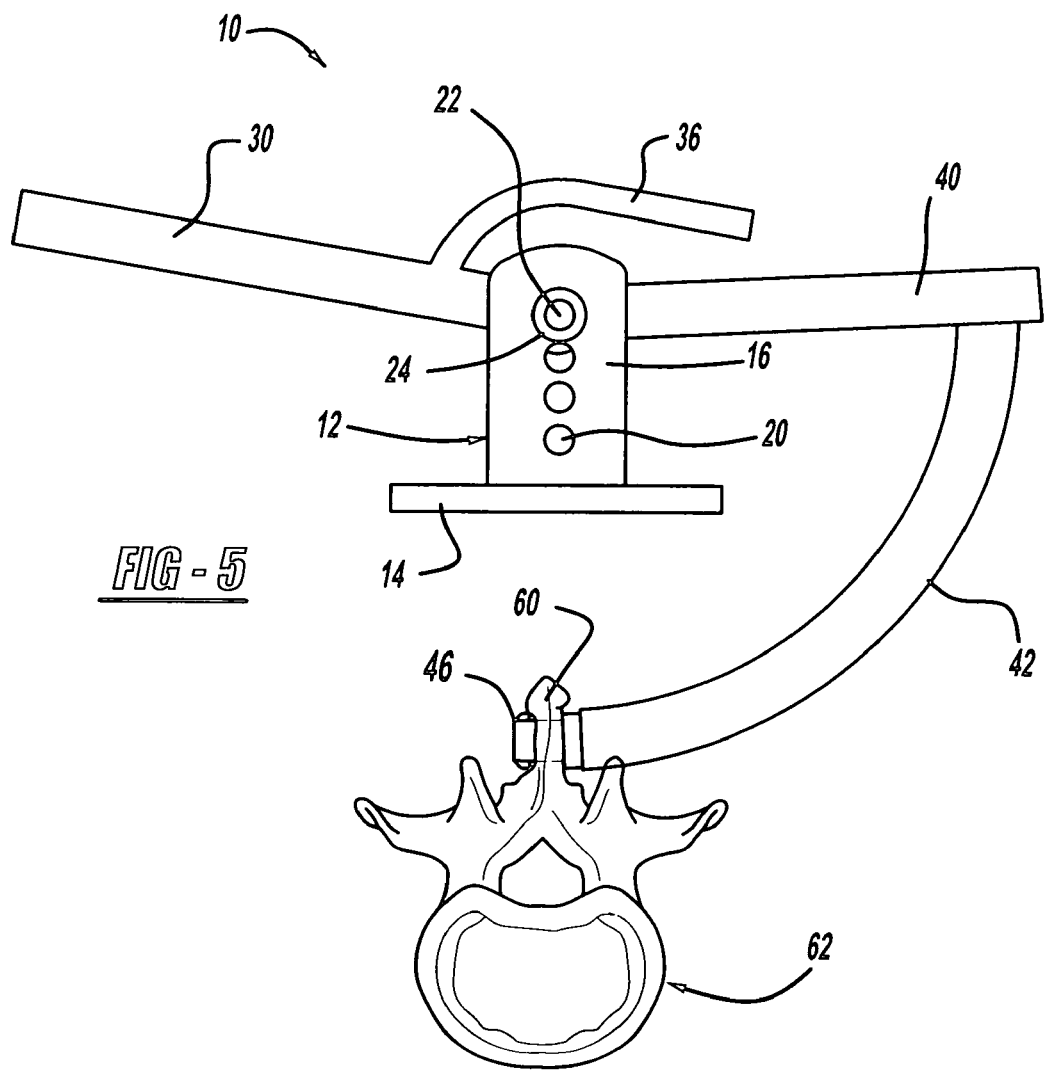
FIG. 5 is a side view of the device depicted in FIG. 1 with the arced trocar rod removed and the cannulated sleeve positioning the spacer between two spinous process.

The arm 30 is then retracted so that the trocar rod 32 is removed from the patient. The arced trocar rod 32 is then removed from the trocar arm 30, as shown in FIG. 5.

Figure 6:
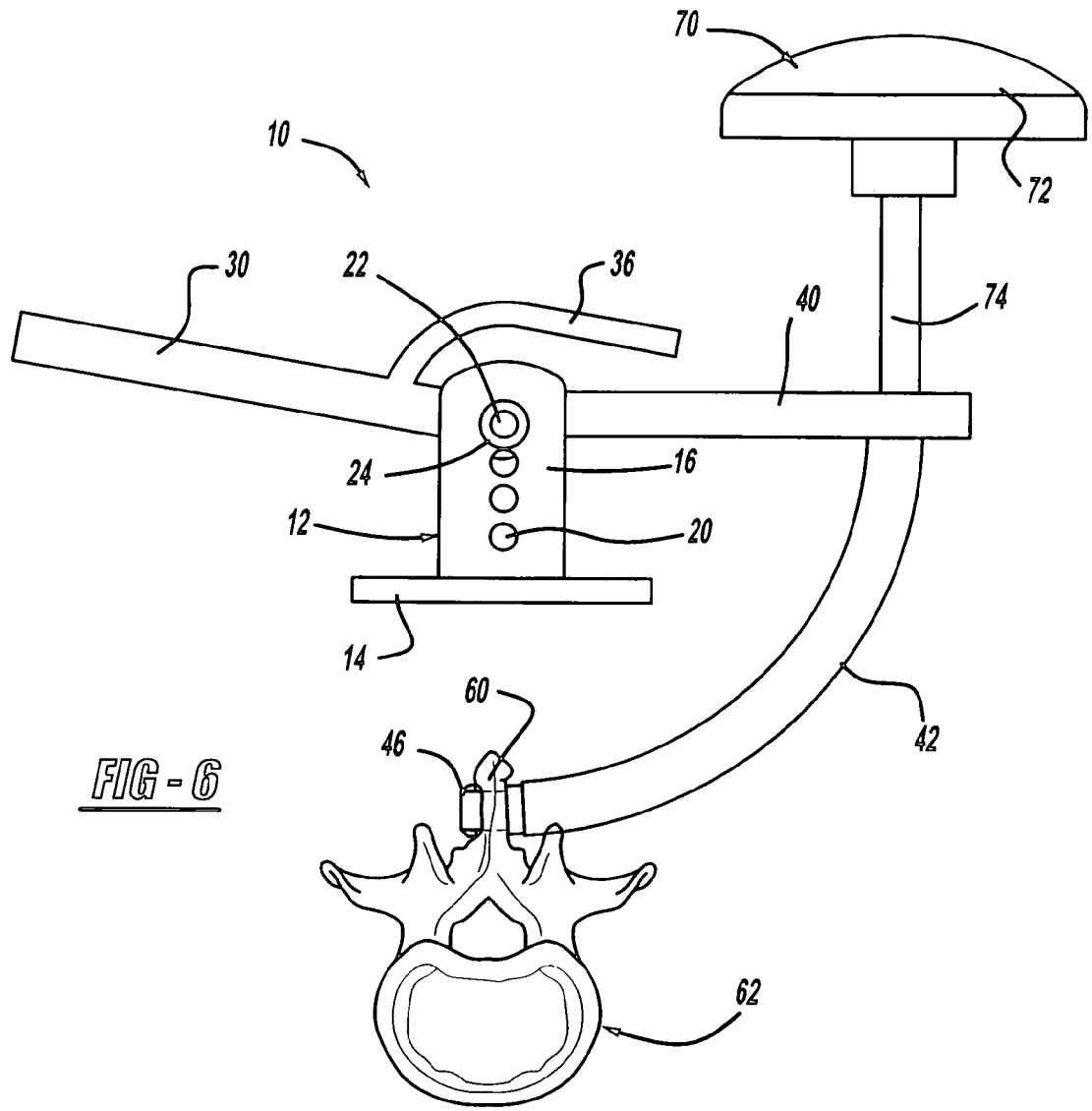
FIG. 6 is a side view of the device depicted in FIG. 1 including a flexible driver positioned within the cannulated sleeve for rotating the interspinous process spacer.

FIG. 6 is a side view of the device 10 including a flexible driver 70 for rotating the spacer 46. The driver 70 includes a handle 72 and a flexible rod 74 mounted thereto. The rod 74 can be made of any suitable material, such as wound steel. The flexible rod 74 is inserted through the bore in the cannulated sleeve 42, and is coupled to the spacer 46. The rod 74 is rotated within the bore of the cannulated sleeve 42 to rotate the spacer 46 so that the fins 52 and 54 lock behind the spinous process 60 of the vertebra 62. The driver 70 is then detached from the spacer 46 and withdrawn from the cannulated sleeve 42. The arm 40 is then raised to remove the spacer 46 from the cannulated sleeve 42 and remove the cannulated sleeve 42 from the patient, where the spacer 46 remains in the patient between the spinous process 60.

Figure 7:
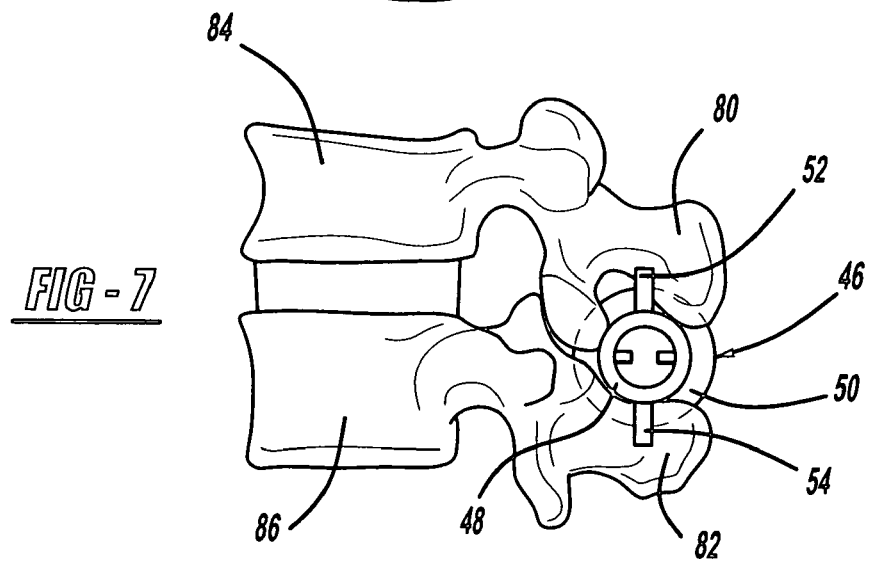
FIG. 7 is a side view of the interspinous process spacer positioned between the spinous process of adjacent vertebrae.

FIG. 7 is a side view of the spacer 46 positioned between the spinous process 80 and 82 of adjacent vertebrae 84 and 86, respectively, to separate the vertebrae 84 and 86 and provide relief for the stenosis. As is apparent, the fins 52 and 54 are positioned on one side of the spinous process 80 and 82 and the end plate 50 is positioned on an opposite side of the spinous process 80 and 82.

Figure 8:
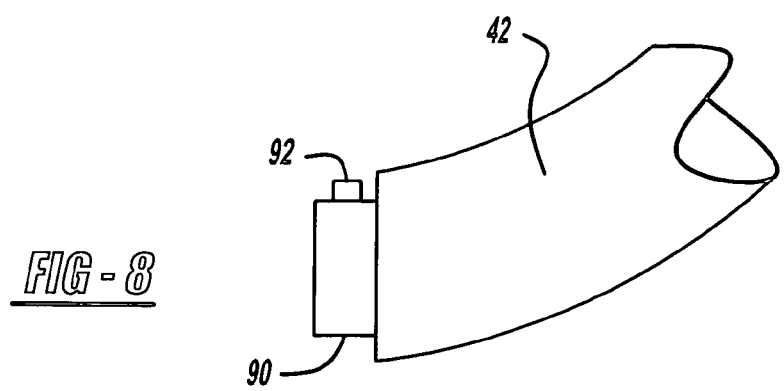
FIG. 8 is a broken-away view of the end of the cannulated sleeve.

The spacer 46 can be attached to the cannulated sleeve 42 and the spacer 46 can be rotated once it is in position between the spinous process 60 in any effective or suitable manner for the purposes described herein. FIG. 8 is a broken-away side view of the cannulated sleeve 42 showing one non-limiting technique for attaching the spacer 46 thereto. The cannulated sleeve 42 includes a narrow-diameter end portion 90 that has an internal diameter that is about the same as the diameter of the internal bore 56 of the spacer 46. A hard stop pin 92 is attached to the narrow-diameter end portion 90.

FIG. 9 is another perspective view of the spacer 46. A cylindrical bore 94 is provide within the end plate 50 that is concentric with the bore 56 and has a larger diameter than the bore 56. An arced slot 96 is provided within the end plate 50 adjacent to the bore 94, and covers about 90° of the circumference of the bore 94. The outer diameter of the end portion 90 is slightly less than the diameter of the bore 94 so that the spacer 46 can slide onto the end portion 90 and be held thereto in a friction type engagement. The end portion 90 can be slightly tapered to facilitate coupling of the spacer 46 to the cannulated sleeve 42. The hard stop pin 92 is positioned at the top end of the slot 96 so that the fins 52 and 54 are properly oriented relative to the insertion direction of the spacer 46 between the spinous process 60.

The spacer 46 includes a pair of opposing elongated tabs 98 and 100 extending partly across the internal bore 56, as shown. The height of the tabs 98 and 100 is such that they allow the arced trocar rod 32 to easily extend therebetween. The surgeon would be able to easily attach the spacer 46 to the narrow-diameter portion 90, and then slide the arced trocar rod 32 through the spacer 46 because this procedure would be performed outside of the patient.

FIG. 10 is a side view of the flexible driver 70 removed from the device 10. The driver 70 includes a slot 106 in the rod 74 at an opposite end to the handle 72. When the flexible driver 72 is extended down the cannulated arm 42, the surgeon aligns the slot 106 with the opposing tabs 98 and 100 so that the tabs 98 and 100 are positioned within the slot 106. The surgeon will then rotate the flexible driver 70, here in a clockwise direction, so that the spacer 46 rotates and the hard stop pin 92 moves along the arced slot 96. When the hard stop pin 92 hits the opposite end of the arced slot 96, the spacer 46 has been rotated 90°, and the fins 52 and 54 will be in the proper orientation for locking the spacer 46 between the spinous process 60. The flexible driver 70 can then be pulled off of the tabs 98 and 100 and be removed from the cannulated sleeve 42. Because the spacer 46 is now locked in placed, the surgeon can raise the arm 40 to detach the spacer 46 from the end portion 90 so that the spacer 46 remains in place.

FIG. 11 is a perspective view of a minimally invasive interspinous process spacer insertion device 120 similar to the device 10 where like elements are identified by the same reference number, according to another embodiment of the present invention. The device 120 includes and trocar arm 122 and two advanced arced trocar rods 124 and 126 coupled thereto for placing two interspinous process spacers between the spinous process of adjacent vertebra.

Various spacer designs can be provided within the scope of the present invention. FIG. 12 is a perspective view of an alternate interspinous process spacer 110 including an end plate 112 and a tapered body portion 114. The body portion 114 includes threads 116 that allow the spacer 110 to be locked between the spinous process.

FIG. 13 is a perspective view and FIG. 14 is a side view of an interspinous process spacer 130, according to another embodiment of the present invention. The spacer 130 includes a tapered body portion 132 having a helical ridge 134 and a center bore 136. An annular rim 138 is attached to the body portion 132 and a coupling portion 140 is attached to the rim 138 opposite to the body portion 132. Opposing wing members 142 and 144 are pivotally attached to the body portion 132. The spacer 130 is placed by rotating the spacer 130 so that the ridge 134 pulls the spacer 130 between the spinous process until the rim 138 is positioned against one side of the spinous process. The wing members 142 and 144 are the extended to lock the spacer to the spinous process.

The foregoing discussion discloses and describes merely exemplary embodiments of the present invention. One skilled in the art will readily recognize from such discussion and from the accompanying drawings and claims that various changes, modifications and variations can be made therein without departing from the spirit and scope of the invention as defined in the following claims.

What is claimed is:

1. An interspinous process spacer insertion device for inserting an interspinous spacer, said device comprising:
   a base portion;
   a trocar arm pivotally mounted to the base portion;
   at least one trocar rod attached to the trocar arm, said trocar rod having an arced configuration, said spacer including an internal bore through which the at least one trocar rod extends; and
   a cannulated arm pivotally mounted to the base portion separately from the trocar arm and a cannulated sleeve mounted to the cannulated arm and having an arced configuration and an internal bore, wherein the interspinous process spacer is attached to an end of the cannulated sleeve opposite to the cannulated arm, said at least one trocar rod extending through the internal bore in the cannulated sleeve.

2. The device according to claim 1 wherein the base portion includes a base plate and at least one stanchion mounted thereto, said cannulated arm and trocar arm being mounted to the at least one stanchion.

3. The device according to claim 1 wherein the base portion includes a height locking member for controlling the depth of the at least one trocar rod.

4. The device according to claim 1 wherein the at least one trocar rod includes a sharp tip.

5. The device according to claim 1 further comprising a flexible driver, said flexible driver extending through the internal bore in the cannulated sleeve when the at least one trocar rod is removed therefrom, and being operable to be coupled to the spacer and rotate the spacer.

6. The device according to claim 5 wherein the cannulated sleeve is cylindrical and includes a narrower diameter end portion that extends into an internal bore of the spacer so as to mount the spacer thereto.

7. The device according to claim 6 wherein the narrow diameter portion includes a hard stop pin and the spacer includes a slot where the hard stop pin is positioned within the slot and controls the rotation distance of the spacer.

8. The device according to claim 5 wherein the spacer includes a pair of opposing tabs and the driver includes a slot where the slot is positioned over the opposing tabs to allow the spacer to be rotated by the flexible driver.

9. The device according to claim 1 wherein the at least one trocar rod is multiple trocar rods for inserting multiple spacers.

10. The device according to claim 1 wherein the spacer includes a cylindrical plate, a cylindrical body portion having a narrower diameter than the cylindrical plate and a securing member.

11. The device according to claim 1 wherein the spacer includes deployable tabs.

12. The device according to claim 1 wherein the spacer is radiolucent.

13. An interspinous process spacer insertion device for percutaneously positioning an interspinous spacer between the spinous process of adjacent vertebra, said device comprising:
- a base portion including at least one stanchion mounted to a base plate;
- a cannulated arm pivotally mounted to the base portion;
- a cannulated sleeve having an arced configuration and an internal bore, said cannulated sleeve being mounted to the cannulated arm, wherein the interspinous process spacer is attached to an end of the cannulated sleeve opposite to the cannulated arm;
- a trocar arm pivotally mounted to the base portion separate from the cannulated arm;
- a trocar rod attached to the trocar arm, said trocar rod having an arced configuration and extending through the internal bore in the cannulated sleeve, said spacer including an internal bore through which the trocar rod extends; and
- a flexible driver extending through the internal bore in the cannulated sleeve when the trocar rod is removed therefrom, said driver being operable to be coupled to the spacer and rotate the spacer, wherein the flexible driver rotates the spacer so that it locks between the spinous process of the vertebra.

14. The device according to claim 13 wherein the spacer includes a cylindrical plate, a cylindrical body portion having a narrower diameter than the cylindrical plate and a retaining member.

15. The device according to claim 13 wherein the base portion includes a height locking member for controlling the depth of the trocar rod.

16. The device according to claim 13 wherein the cannulated sleeve is cylindrical and includes a narrower diameter end portion that extends into an internal bore of the spacer so as to mount the spacer thereto.

17. The device according to claim 16 wherein the narrow diameter portion includes a hard stop pin and the spacer includes a slot where the hard stop pin is positioned within the slot and controls the rotation distance of the spacer.

18. The device according to claim 13 wherein the spacer includes a pair of opposing tabs and the driver includes a slot where the slot is positioned over the opposing tabs to allow the spacer to be rotated by the flexible driver.

\* \* \* \* \*